United States Patent [19]

Kurihara et al.

[11] Patent Number: 5,576,182

[45] Date of Patent: Nov. 19, 1996

[54] ANTI-MUCUS GLYCOPROTEIN MONOCLONAL ANTIBODY

[75] Inventors: Makoto Kurihara, Isehara; Kazuhiko Ishihara, Sagamihara; Kyoko Hotta, Tokyo; Hiromi Tanaka; Shiro Shimauchi, both of Isehara, all of Japan

[73] Assignee: Kanto Kagaku Kabushiki Kaisha, Tokyo, Japan

[21] Appl. No.: 373,220

[22] PCT Filed: May 26, 1994

[86] PCT No.: PCT/JP94/00838

§ 371 Date: Jan. 19, 1995

§ 102(e) Date: Jan. 19, 1995

[87] PCT Pub. No.: WO94/28158

PCT Pub. Date: Dec. 8, 1994

[30] Foreign Application Priority Data

May 26, 1993 [JP] Japan ..................... 5-159891

[51] Int. Cl.$^6$ ..................... C12P 21/08; C12N 5/20; G01N 33/577

[52] U.S. Cl. ............. 435/7.9; 435/7.92; 435/70.21; 435/240.27; 435/960; 436/505; 436/64; 530/387.5; 530/388.2

[58] Field of Search .................. 435/7.9, 7.92–7.95, 435/960, 240.27, 70.21, 172.2; 436/503, 530–531, 64, 63; 530/387.5, 387.7, 388.1, 388.2, 395, 808, 863; 424/85.8, 85.91

[56] References Cited

U.S. PATENT DOCUMENTS 5,183,756  2/1993  Schlom ..................... 435/240.27

OTHER PUBLICATIONS

Ghanei et al., "Murine Monoclonal Antibody Against Differential Antigenes of the Gastric Mucosa Passing Through Paraffin," *Verh. Dtsch. Ges. Path.* 73, 665 (1989) with English translation.
Dekkert et al. (1989) *Jour. Biol. Chem.* 264 (18) pp. 10431–10437.
Ishihara (1993) *Hybridoma* 12 (5): pp. 609–620.
Tatematsu et al. (1993) *Acta Path. Japonica* 43:500–506.
Lupo et al. (1993) *Euro. J. Cell Biology* 61, pp. 150–159.
Burtin et al. (1977) *Int. J. Cancer* 19:pp. 634–641.
Katsuyama et al. (1977) *J. Histochem. and Cytochem* 26 (4) pp. 233–250.
Ota et al. (1991) *Histochem. Journal* 23, pp. 22–28.
Katsuyama et al. (1989) *Byori to Rinsho* 7:pp. 1217–1224 partial English translation.
Matsuzawa et al. (1992) *Human Pathology* 23 (8) pp. 925–933.
Köhler et al. (1975) *Nature* 256:pp. 495–497.
Ohara et al. (1986) *Comp. Biochem. Physiol.* 83B: pp. 273–275.
Klebe et al. (1981) *Somatic Cell Genetics* 7 (4) pp. 473–488.
Schulman et al. (1978) *Nature* 276:pp. 269–270.
D. Carlson (1968) *Jour. Biol. Chem.* 243 (3) pp. 616–626.
Sweeley et al. (1963) *Gas. Chrom. of Sugars* 85: pp. 2497–2507.
F. Hanisch et al, "Monoclonal Antibody 2B5 Defines a Truncated O. Glycan . . . on Mucins from Deep Gastric and Duodonal Glands . . . ," *Cancer Res.* 53; 4791–4796, (Oct. 1993).
N. Hughes et al, "Phenotypic identity of gastric mucous neck cells and mucous cells of cardiac, pyloric and Brunner's glands," *J. Clin. Pathol.* 47: 53–57, (1994).
S. Vetsuki et al, "Establishment and Characterization of Monoclonal Antibodies to Carbohydrate Antigens on . . . Gastric Cancer Kato–III," *Hybridoma* 11: 425–435 (1992).
H. Zola, *Monoclonal Antibodies: A Manual of Techniques* by CRC Press, Inc. (Boca Raton), published 1987, p. 8.

Primary Examiner—Carol A. Spiegel
Attorney, Agent, or Firm—Birch, Stewart, Kolasch & Birch, LLP

[57] ABSTRACT

An IgM class monoclonal antibody which specifically reacts with mucus glycoproteins produced by human gastric gland-type mucous cells is provided. By performing immunohistochemical staining using a labeled derivative of the monoclonal antibody, human gastric gland-type mucous cells as well as mucus secreted by these cells can be specifically stained. The monoclonal antibody can also be used for the analysis of gastric gland-type mucous cell-derived mucus glycoproteins in human body fluids as well as for the examination or diagnosis of cancer.

5 Claims, No Drawings

ANTI-MUCUS GLYCOPROTEIN MONOCLONAL ANTIBODY

FIELD OF THE INVENTION

The present invention relates to a novel monoclonal antibody which can be used in assays for human gastric gland-type mucus. Thus, the present invention provides a novel antibody which has strong affinity for human gastric gland mucous cells as well as for the mucus secreted thereby but which has cross-reactivity neither with human gastric surface mucous cells nor with the mucus secreted thereby.

BACKGROUND ART

The mucus-secreting cells present in the epithelium of alimentary tract mucosae including gastric mucosa are considered to be involved in the maintenance of gastrointestinal functions by synthesis, followed by secretion, of mucus. Gastric mucus in particular is viewed as one of the important defense factors to protect the gastric mucosa from attack by such factors as gastric acid and pepsin.

The mucus production in the human stomach is effected by surface mucous cells (covering epithelial cells) present in the gastric mucosa surface epithelium and gastric gland mucous cells present in the deep part of the gastric gland. Recent years have seen attempts to differentiate individual mucus species produced by these mucous cells. A histochemical staining method has been developed which is specific for the sugar components peculiar to the respective mucus species of surface mucous cells and gland mucous cells, and hence is able to differentiate between them. Thus, the mucus found in the surface mucous cells can be specifically stained by the galactose oxidase-cold thionin Schiff (GOCTS) reaction, while in the gland mucous cells mucus classified as class III by the Concanavalin A paradoxical staining method (Katsuyama, T. and Spicer, S. S. (1978), J. Histochem. Cytochem. 26, 233–250) is found to be specifically localized (Ota, H. et al. (1991), Histochemical J. 23, 22–28). Mucus gel layer covering the surface epithelium of the gastric mucosa has been proved to be a laminar structure of alternating layers of the GOCTS-reactive mucus and the Class III mucus, and the mucus gel layer has been found to contain both mucus species from surface mucous cells and gland mucous cells (Ota, H. et al. (1991), Histochemical J. 23, 22–28).

Katsuyama et al. have elucidated that in normal tissues class III mucus can be found only in the limited glandular epithelia of the alimentary tract ranging from the cardiac glands of the esophagus through the cardiac glands, mucous neck cells and pyloric glands of the stomach, Brunner's glands of the duodenum, the mucous glands of the papilla of Vater and the mucous glands of the pancreatic duct in the head of the pancreas, whereas it can be demonstrated with high incidence in such tumor tissues as in cholecystic adenoma, gallbladder cancer and pancreatic duct cancer (Katsuyama et al. (1989), Byori to Rinsho 7, 1217–1224). Furthermore, Matsuzawa et al. has found, referring to the relationship between metaplasia and cancer, that such forms of tissue as found in the gastric mucosa where strongly GOCTS-positive mucus is found in the surface epithelium of the mucosa and class III mucus is localized in the deep part thereof cannot be seen in normal pancreatic duct tissues but frequently in pancreatic duct tissues with metaplasia or carcinoma (Matsuzawa, K. et al. (1992), Human Pathology 23, 925–933). These study results suggest that data for the diagnosis of cancer diseases or possible cancerization can be presented by determining the gastric type mucus secreted into the body fluid, particularly the gastric gland-type mucus.

As for the specific detection of the human gastric gland-type mucus, no other methods than the above-mentioned Concanavalin A paradoxical staining method have been known to date. The known detection method, however, cannot quantitatively determine the gastric gland-type mucus because of its poor reproducibility of staining and also because of the drawback that the method can be applied only to fixed specimens and hence cannot be applied to the determination of secreted or solubilized mucus.

DISCLOSURE OF THE INVENTION

As a result of their intensive studies of monoclonal antibodies capable of recognizing the human gastric gland-type mucus, the present inventors have now succeeded in obtaining a hybridoma producing a novel monoclonal antibody with high specificity for human gastric gland-type mucous cells and for the mucus secreted therefrom, as well as the monoclonal antibody, by using as antigen for immunization mucus glycoproteins (mucins) which are the major components of the mucus.

Thus, the present invention provides, as described in 1.–5. below, a novel monoclonal antibody and hybridoma, as well as use of the monoclonal antibody for the analysis of gastric gland-type mucous cell-derived mucus glycoproteins contained in body fluids.

1. An IgM class monoclonal antibody which specifically reacts with mucus glycoproteins produced by human gastric gland-type mucous cells.
2. The monoclonal antibody of 1. wherein the IgM class monoclonal antibody is produced by a hybridoma deposited in the National Institute of Bioscience and Human-Technology (NIBH), Agency of Industrial Science and Technology 1-3, Higashi 1-chome, Tsukuba-shi, Ibaraki-ken 305, Japan, on Apr. 28, 1993 with the accession number P-13622.
3. A hybridoma which produces an IgM class monoclonal antibody with specific reactivity with mucus glycoproteins produced by human gastric gland-type mucous cells.
4. A hybridoma deposited in the National Institute of Bioscience and Human Technology (NIBH), Agency of Industrial Science and Technology with the accession number P-13622.
5. Use of the monoclonal antibody of 1. for the analysis of gastric gland-type mucous cell-derived mucus glycoproteins contained in human body fluids.

The present invention thus relates to a monoclonal antibody useful for the staining of gland mucous cells (i.e. cardiac gland cells, mucous neck cells and pyloric gland cells) of the human gastric mucosa as well as mucous cells producing human gastric gland-type mucus (e.g. Brunner's glands of the duodenum, gastric gland-type metaplastic cells and gastric gland-type tumor cells). Furthermore, the present invention relates to a monoclonal antibody useful for the determination of mucus glycoproteins secreted by the above-mentioned gastric gland-type mucous cells. More particularly, immunohistochemical staining with the monoclonal antibody of the present invention or a labeled derivative thereof permits specific staining of human gastric gland-type mucous cells as well as the mucus secreted thereby, and ELISA (enzyme-linked immunosorbent assay) therewith permits the analysis, both qualitative and quantitative, of gastric gland-type mucous cell-derived mucus glycoproteins contained in human body fluids, e.g. gastric juice, pancreatic juice, blood and sputum. The monoclonal antibody of the present invention can also be used for the examination and diagnosis of cancer.

The hybridoma which produces the monoclonal antibody of the present invention may be obtained by any conventional method, e.g. the method of Koehler and Milstein (Koehler, G. and Milstein, C. (1975) Nature 256, 495–497), using mucus glycoprotein prepared by any appropriate method. Thus, the above-mentioned mucus glycoprotein is used to immunize a mouse and splenic cells from the mouse are fused with murine myeloma cells. From among the resultant hybridomas can be selected and isolated a hybridoma which produces and secretes the desired antibody. Methods of preparing the above-mentioned hybridoma and monoclonal antibody of the present invention, as well as characteristics of the monoclonal antibody, will now be described in the following.

A. Isolation and Purification of Antigen:

As antigen for immunization there may be used extracts from human or non-human mammalian gastric mucosa or Brunner's glands. Preferably, mucus glycoproteins obtained from these extracts are purified prior to their use. Thus, for example, the mucus glycoprotein extracted and purified from rat gastric mucosa in accordance with the method of Ohara et al. (Ohara, S. et al. (1986), Comp. Biochem. Physiol. 83B, 273–275) is used. In the examples described below, the extracts from rat gastric mucosa were fractionated by gel filtration and fractions corresponding to molecular weights not lower than 1,500,000 are collected and subjected to CsCl equilibrium density gradient centrifugation to afford glycoprotein fractions (mucus glycoprotein-containing fractions). The thus obtained mucus glycoprotein was used as immunizing antigen.

B. Immunization of mice

As animals to be immunized, there may preferably be used four to eight-week-old BALB/c mice, although mice of other strains may also be used. Immunization schedule and antigen concentration are selected such that an adequate quantity of antigen-stimulated lymphocytes are formed. Thus, for example, mice are intraperitoneally administered with 100 µg/animal of the above-described mucus glycoprotein together with appropriate adjuvant. Subsequently, the animals were administered several times at intervals of several days or weeks with the same antigen as used for the first immunization. After the second immunization, blood samples are taken from the eyeground vein to assay them for antibody titre. Antibody titre may preferably be measured by ELISA.

C. Cell Fusion

The spleen is excised from the immunized mouse and an aqueous suspension of single splenic cells is prepared therefrom. The suspension is subjected to cell fusion with murine myeloma cells using an appropriate fusogenic agent. As a preferred example of such fusogenic agent there may be mentioned polyethylene glycol of mean molecular weight 400–6,000, although any other fusogenic agents known in the art may also be used (Klebe, R. J. and Mancuso, M. G. (1981), Somat. Cell. Genet., 7, 473–488). In the examples described below there was used polyethylene glycol 4,000 (E. Merck; Cat. No. 9727). Those myeloma cells are preferably used which are derived from the same animal species as the animal used for the preparation of splenic cells and which are not to produce any antibody. In the examples described below, there were used 8-azaguanine-resistant mouse myeloma cells Sp2/O-Ag14 (Shulman, M. et al. (1978) Nature 276, 269–270). It is preferred to use splenic cells and myeloma cells at a cell count ratio of about 20:1—about 5:1.

D. Selection of Fused Cells

In a separate container, the mixture obtained in C. above, i.e. the mixture of unfused splenic cells, unfused myeloma cells and fused cells is cultured for an appropriate period in selection medium which does not support the growth of the unfused cells, thereby to kill the unfused cells. As such medium there may be used one which does not support the growth of unfused myeloma cells which are drug-resistant (e.g. 8-azaguanine-resistant), for example, HAT medium. Since unfused splenic cells are non-tumor cells, unfused splenic cells and unfused myeloma cells die in such selection medium after a certain period. Fused cells are viable in such selection medium because they have both tumor characteristic of their parental myeloma cells and characteristics of splenic cells.

E. Identification of Antibody Produced by Hybridoma in Each Container (Screening)

The culture supernatant is sampled from each of the wells with respect to which hybridoma has been confirmed to be formed by the cultivation in D. above, and assayed for the presence of immunoreactivity with gastric mucus glycoprotein. Such screening may preferably be performed by ELISA, for example. Immunoreaction-positive samples are further screened for specific recognition of gastric gland mucous cells and the mucus secreted thereby. Such screening may preferably be carried out, for example, by immunohistochemical staining using sections of fixed gastric mucosa specimens.

F. Cloning of Hybridoma Producing the Desired Antibody and Production of the Antibody The immunoreaction-positive cell suspension obtained in E. above is then cloned by any appropriate method, for example, by the limiting dilution method, whereafter the desired antibody may be obtained in either one of the two ways. One way involves cultivation of hybridoma in any appropriate medium for a certain period, followed by isolation from the culture supernatant of the monoclonal antibody produced by the hybridoma. The other way involves intraperitoneal inoculation of a syngeneic or semi-syngeneic mouse with hybridoma. In the latter case, the desired monoclonal antibody produced by the hybridoma may be isolated after a certain period from the blood or ascites fluid of the inoculated mouse.

G. Purification of Monoclonal Antibody

From the hybridoma culture supernatant, or from the mouse blood or ascites fluid, as obtained in F. above, the monoclonal antibody of the present invention can be purified by any biochemical purification method widely used in the art. Thus, for example, such purification may preferably be carried out by combining different purification procedures such as ammonium sulfate salting out, ion-exchange column chromatography, molecular sieve column chromatography or affinity column chromatography.

H. Labeling of Monoclonal Antibody and Use of the Labeled Monoclonal Antibody

The thus purified monoclonal antibody may be labeled by any biochemical means widely used in the art with peroxidase, alkaline phosphatase, biotin etc. Labeling may be performed by linking product from periodate oxidation of the enzyme to the antibody or by combining the enzyme and antibody together using glutaraldehyde as crosslinking agent. The thus obtained labeled monoclonal antibody can be conveniently applied to immunohistochemical staining or ELISA-based sandwich assay. As for the ELISA method, the quantitative determination of gastric gland-type mucous cell-derived mucus glycoprotein contained in a sample may be performed, for example, by adsorption of the monoclonal antibody of the present invention as primary antibody onto each well of an ELISA plate, followed by further adsorption of a material which is not involved in the reaction, e.g. skim milk, onto the adsorbed sites of each well. Sample solution is then added to each well and the wells are washed. Aliquots of labeled monoclonal antibody solution of appropriate concentrations are added to the wells, followed, after washing of the wells, by addition of a solution of substrate for the enzyme used in the ELISA.

I. Reactivity of Monoclonal Antibody with Antigen

The antigen recognizing site of the monoclonal antibody according to the present invention can be examined by studying the reactivity of the monoclonal body with compounds of known structures. The present inventors subjected crossreacting pig gastric mucus protein (Sigma) to decomposition treatment by conventional biochemical means and components with antigenic activity were separated and isolated from the decomposition products and analyzed by conventional physicochemical means. The antigenic activity may be conveniently measured by a Competitive ELISA which is an application of the inhibition assay to the ELISA.

The present invention will now be further illustrated by way of examples, to which the present invention is by no means limited.

Example 1

(1) Preparation of antigen for immunization

Stomachs were excised from female SD rats weighing 250–300 g (Japan SLC, Inc.) and the gastric mucosae were collected therefrom by scraping and then subjected to extraction with 50 mM Tris-HCl buffer, pH 7.2, containing 2% of the non-ionic surface active agent TRITON X-100 (polyethylene glycol mono p-isooctylphenyl ether). The extracts were subjected to gel filtration using a Bio-Gel A, agarose gel beads, 1.5 m column (Bio-Rad Laboratories) to collect the eluted fractions of molecular weights not lower than 1,500,000. These fractions were further subjected to CsCl equilibrium density gradient centrifugation (N.B.) to obtain purified glycoprotein antigen (mucus glycoprotein fraction) of density 1.4±0.4 g/ml, using a fraction collector.

N.B. "CsCl equilibrium density gradient centrifugation" was carried out under the following conditions:

| Centrifugation | $1.5 \times 10^5$ g |
|---|---|
| Temperature | 10° C. |
| Period | 85 hours |
| Apparatus | Model 72P; Rotor : RPS-40T (Hitachi, Ltd.) |

(2) Preparation of splenic cells from immunized mice

Four-week-old female BALB/c mice were immunized intraperitoneally with 50 μl of Freund's complete adjuvant (Difco, Laboratories) and 100 μg/animal of the purified mucus glycoprotein antigen obtained by the procedure mentioned above (hereinafter referred to as the purified mucus glycoprotein antigen). The animals were then intraperitoneally administered, at 3-week intervals for boosting, with 50 μl of Freund's incomplete adjuvant (Difco, Laboratories) and 100 μg/animal of the same purified mucus glycoprotein antigen as used for the first immunization. On the third or fourth day after each boosting, blood samples were taken from the eyeground vein and analyzed for antimucus glycoprotein antibody in the sera by the ELISA method as described below.

ELISA: The purified mucus glycoprotein antigen was dissolved in 0.05M sodium carbonate-sodium hydrogen carbonate buffer, pH 9.6, at a concentration of 2 μg/ml and the same buffer was used to prepare two-fold serial dilutions. 100 μl aliquots of each dilution was added to wells of a microplate adapted for use in ELISA (Corning) and the wells were allowed to stand overnight at 4° C. Each well was washed three times with 0.05% of the non-ionic surface active agent TWEEN-20, polyoxyethylene sorbitan monolaurate, (Nacalai Tesque, Inc., Japan) in PBS (PBS-TWEEN), filled with 2% skim milk in PBS, and then allowed to stand for 1 hour. The wells were washed three times with PBS-TWEEN and a 1,000-fold dilution of mouse serum sample was dispensed in 100 μl aliquots into the wells. After incubation for 1 hour, the wells were washed three times with PBS-TWEEN, and 100 μl of a 10,000-fold dilution in PBS of peroxidase-labeled goat anti-mouse immunoglobulins antibody (Tago, Inc.) was added as secondary antibody to each well and allowed to stand for 1 hour. The wells were washed three times with PBS-TWEEN and 100 μl of an ABTS(2,2'-azino-di[3-ethylbenzthiazoline sulfonate (6)])-$H_2O_2$ peroxidase substrate solution (Kirkegaard & Perry Laboratories) was added to each well. After reaction at room temperature for 30 minutes, the optical density at 415 nm was measured for each well using a microplate reader. Those mouse sera which developed a color in dependence on the dose of the mucus glycoprotein were judged to be antibody-positive.

Spleens were excised from those mice which were thus judged to be positive with respect to antibody against the purified mucus glycoprotein antigen and an aqueous suspension of single splenic cells was prepared therefrom for use in cell fusion.

(3) Preparation of mouse myeloma cells 8-azaguanine-resistant mouse myeloma cells Sp2/O-Ag14 were cultured at 37° C. in normal medium [RPMI 1640 (Nissui Pharmaceutical Co., Ltd. ) (10.2 g/l) medium supplemented with sodium hydrogen carbonate ( 2.2 g/l), L-glutamine (0.3 g/l), gentamycin (40 mg/l) and fetal calf serum (10% V/V)], using a carbonic acid gas incubator.

(4) Cell fusion and cultivation of hybridomas

The splenic cells and mouse myeloma cells Sp2/O-Ag14 obtained above were mixed together at a cell count ratio of 10:1 and then subjected to cell fusion while adding a fusing solution [polyethylene glycol 4,000 (0.5 g) in dimethyl sulfoxide (0.05 ml) and PBS (0.5 ml)] to the mixture with gentle stirring. After incubation at 37° C. for 90 seconds, a medium [RPMI 1640 (Nissui Pharmaceutical Co., Ltd. ) (10.2 g/l) medium supplemented with sodium hydrogen carbonate (2.2 g/l), L-glutamine (0.3 g/l) and gentamycin (40 mg/l)] was slowly added thereto to make up the total fluid volume to 40 ml. After centrifugation at 1,100 rpm for 10 minutes, the supernatant was removed and HAT (hypoxanthine aminopoterin thymidine) medium [RPMI 1640 (Nissui Pharmaceutical Co., Ltd. ) (10.2 g/l) medium supplemented with sodium hydrogen carbonate (2.2 g/l), L-glutamine (0.3 g/l), gentamycin (40 mg/l), fetal calf serum (20% V/V), hypoxanthine (100 μmol/l), aminopterin (0.4 μmol/l) and thymidine (16 μmol/l)] to suspend the cells therein in a gentle manner. The suspension was added to each well of a 96-well culture plate and the suspension was cultivated in an incubator containing 5% carbonic acid gas.

(5) Screening and cloning

From the wells of the above-described 96-well culture plate where the growth of fused cells in the form of colonies were observed, there were taken aliquots of each culture supernatant. Screening for hybridomas producing antibody capable of reacting with the purified mucus glycoprotein antigen was performed by the ELISA as described below.

There were thus selected HIK-22 and HIK-108. Further screening was carried out with respect to the antibodies produced by HIK-22 and HIK-108, using the immunohistochemical staining method as mentioned below. There was thus selected HIK-108 as hybridoma producing an antibody with reactivity with gastric gland mucous cells as well as mucus secreted thereby. The HIK-108 was subcultured for one week in HT (hypoxanthine thymidine) medium [RPMI 1640 (Nissui Pharmaceutical Co., Ltd.) (10.2 g/l) medium supplemented with sodium hydrogen carbonate. (2.2 g/l), L-glutamine (0.3 g/l), gentamycin (40 mg/l), fetal calf serum (15% V/V), hypoxanthine (100 µmol/l) and thymidine (16 µmol/l)] and for another week in normal medium [RPMI 1640 (Nissui Pharmaceutical Co., Ltd.) (10.2 g/l) medium supplemented with sodium hydrogen carbonate (2.2 g/l), L-glutamine (0.3 g/l), gentamycin (40 mg/l) and fetal calf serum (10% V/V)], and two limiting dilution subclonings were conducted to give three hybridomas, HIK-1081, HIK-1082 and HIK-1083. These hybridomas were individually subcultured for 4 weeks in the normal medium and each hybridoma culture supernatant was analyzed by the ELISA method as mentioned below. There was thus selected HIK-1083 (deposited in the National Institute of Bioscience and Human-Technology (NIBH), Agency of Industrial Science and Technology with the accession number P-13622) as the hybridoma giving the culture supernatant showing the most intense color development.

ELISA: The purified mucus glycoprotein antigen was dissolved in 0.05M sodium carbonate-sodium hydrogen carbonate buffer, pH 9.6, at a concentration of 1 µg/ml. 100 µl of the solution was added to each well of a microplate adapted for use in ELISA (Corning) and was allowed to stand overnight at 4° C. Each well was washed three times with 0.05% TWEEN 20 in PBS (PBS-TWEEN), filled with 2% skim milk in PBS and then allowed to stand for 1 hour. The wells were washed three times with PBS-TWEEN and 100 µl/well of hybridoma culture supernatant obtained in (5) above was added to each well. After incubation for 1 hour, the wells were washed three times with PBS-TWEEN, and 100 µl/well of a 10,000-fold dilution in PBS of peroxidase-conjugated goat anti-mouse immunoglobulins antibody (Tago, Inc.) was added as secondary antibody to each well and allowed to stand for 1 hour. The wells were washed three times with PBS-TWEEN and 100 µl of an ABTS-$H_2O_2$ peroxidase substrate solution (Kirkegaard & Perry Laboratories) was added to each well. After reaction at room temperature for 30 minutes, the optical density at 415 nm was measured for each well using a microplate reader. Those wells were selected which showed a more intense color development than the wells treated in the same manner as described above except that the myeloma cell culture supernatant obtained in (3) above was added instead of the hybridoma culture supernatant. The samples corresponding to the so selected color-developing wells were judged to be positive.

Immunohistochemical staining: Human gastric mucosa was fixed with formalin, embedded in paraffin and sliced into 4 µm-thick sections using a microtome. Each of the thus prepared sections was fixed on a slide glass. Each slide glass was dipped in xylene for deparaffinization and then in methanol containing 0.3% hydrogen peroxide for 30 minutes and then washed by dipping in PBS for 30 minutes. Subsequently, 10% rabbit normal serum (Nichirei Corporation) was applied to the thus washed section on each slide glass. After incubation for 1 hour, the sections were washed in PBS. Samples of hybridoma culture supernatant were applied onto the washed sections. After incubation for 1 hour, the sections were washed in PBS. Biotin-labeled rabbit anti-mouse IgG+IgA+IgM (H+L) (Nichirei Corporation) was applied onto each washed section. After incubation for 1 hour, the sections were washed in PBS. Peroxidase-conjugated streptavidin (Nichirei Corporation) was then applied onto each washed section. After incubation for 1 hour, the sections were washed in PBS. Subsequently, each washed section was dipped for about 4 minutes in 0.05M Tris-HCl buffer, pH 7.6, containing 0.02% diaminobenzidine (Dojindo Laboratories) and 0.005% aqueous hydrogen peroxide, for color development.

(6) Identification of isotype

The monoclonal antibody according to the present invention was analyzed for globulin class by ELISA using an isotyping kit (PharMingen). Thus, monoclonal rat anti-mouse $IgG_1$, monoclonal rat anti-mouse $IgG_{2a}$, monoclonal rat anti-mouse $IgG_{2b}$, monoclonal rat anti-mouse $IgG_3$, monoclonal rat anti-mouse IgM, monoclonal rat anti-mouse IgA, monoclonal rat anti-mouse IgL (κ) and monoclonal rat anti-mouse IgL (λ) were used and each reagent was diluted 1:5 with coating buffer. Each 50 µl/well of the dilutions was poured into the wells of a microplate adapted for use in ELISA (Corning) and the wells were allowed to stand overnight at 4° C. Each well was washed three times with 0.05% TWEEN 20 in PBS (PBS-TWEEN), filled with 2% skim milk in PBS and then allowed to stand for 1 hour. The wells were washed three times with PBS-TWEEN and culture supernatant from a 3-day culture of HIK-1083 (Accession number P-13622) in a normal medium [RPMI 1640 (Nissui Pharmaceutical Co., Ltd. ) (10.2 g/l) medium supplemented with sodium hydrogen carbonate (2.2 g/l), L-glutamine (0.3 g/l), gentamycin (40 mg/l) and fetal calf serum (10% V/V)] was dispensed in 50 µl portions into the wells. After 1-hour incubation, the wells were washed three times with PBS-TWEEN and 50 µl of an alkaline phosphatase-labeled polyclonal rat anti-mouse Igs reagent was added to each well. The wells were allowed to stand for 1 hour and then washed three times with PBS-TWEEN. To each well was added 50 µl of a substrate solution prepared by dissolving one pNPP (p-Nitrophenylphosphate) tablet in 5 ml of a solvent for the substrate.

After incubation at room temperature for 30 minutes, the microplate was visually observed to find that the only two wells pretreated with the monoclonal rat anti-mouse IgM reagent and the monoclonal rat anti-mouse IgL (κ) reagent, respectively, showed an intense-yellow coloration, the other wells being colorless and transparent. On the basis of these results, the monoclonal antibody of the present invention was identified as an IgM antibody with the light chain being a κ chain.

(7) Preparation of monoclonal antibody

Six-week-old female BALB/c mice weighing 19–21 g were intraperitoneally administered with 0.5 ml/animal of 2,6,10,14-tetramethylpentadecane (pristane) and then raised for 10–14 days. These animal were then intraperitoneally administered with $5 \times 10^6$ cells/animal of the above-mentioned hybridoma strain HIK-1083 (Accession number P-13622). After 10–21 days, the accumulated ascites fluid was collected and subjected to centrifugation (12,000 rpm/ 20 minutes/4° C.).

The supernatant was then separated and ammonium sulfate was added to 40% saturation for salting out. The mixture was subjected to centrifugation (12,000 rpm/20 minutes/4° C.). The resulting sediment was dissolved in PBS and then dialyzed against PBS at 4° C. for 2 days and the dialyzate was loaded onto an affinity column as follows. Thus pig gastric mucus glycoprotein (Sigma) was dissolved in 0.1M phosphate buffer, pH 7.8, containing 0.5M NaCl and the solution was mixed with CNBr-Activated SEPHAROSE 4B, agarose gel beads (Pharmacia) swelled with the same buffer. A column was packed with the mixture and then washed with the same buffer. The components of the above-mentioned dialyzate were adsorbed onto the column and the so adsorbed dialyzate components were eluted with 0.2M glycine-HCl buffer, pH 2.0, containing 0.5M NaCl. 3M Tris-HCl buffer, pH 8.5, was added to the eluate and the resulting mixture was used for the following labeling reaction with horseradish peroxidase.

(8) Labeling of monoclonal antibody

Horseradish peroxidase (Amano Pharmaceutical Co., Ltd.) was dissolved in distilled water and a 0.1M aqueous solution of sodium metaperiodate was added and the mixture was incubated for 10 minutes. Ethylene glycol was added to the reaction solution and the mixture was desalted using a SEPHADEX G-25, dextran gel beads bridged with epichlorohydrin column (Pharmacia) to prepare a periodate-processed peroxidase solution. The periodate-processed peroxidase solution was mixed with the above-mentioned monoclonal antibody purified from the mouse ascites fluid by using the affinity column. The mixture was incubated at room temperature for 2 hours and after a 0.1M aqueous solution of sodium borohydride was added the mixture was incubated for a further 2 hours. The resulting reaction solution was fractionated into 35 fractions by using a SEPHACRYL S-200 HR, allyl dextran gel beads bridged with N,N'-methylene bis-acrylamide (Pharmacia) and each fraction was analyzed by the ELISA method as described below. Four fractions which gave color development were combined and frozen before storage.

ELISA: The purified mucus glycoprotein antigen was dissolved in 0.05M sodium carbonate-sodium hydrogen carbonate buffer, pH 9.6, at a concentration of 1 µg/ml. 100 µl of the solution was added to each well of a microplate adapted for use in ELISA (Corning) and was allowed to stand overnight at 4° C. Each well was washed three times with 0.05% TWEEN 20 in PBS (PBS-TWEEN), filled with 2% skim milk in PBS and then allowed to stand for 1 hour. The wells were washed three times with PBS-TWEEN and the column eluate sample (each fraction) was dispensed in 100 µl aliquots into the wells, followed by incubation for 1 hour. The wells were washed three times with PBS-TWEEN and 100 µl of an ABTS-$H_2O_2$ peroxidase substrate solution (Kirkegaard & Perry Laboratories) was added to each well. After incubation at room temperature for 30 minutes, the optical density at 415 nm was measured for each well using a microplate reader.

Example 2

Antigenic specificity of monoclonal antibody (1) Confirmation of antigenic specificity by immunohistochemical staining The reactivity of the monoclonal antibody obtained in Example 1 with human gastric mucosa was studied by immunohistochemical staining. Thus human gastric and duodenal mucosae were fixed with formalin, embedded in paraffin and sliced into 4 µm-thick sections using a microtome. Each of the thus prepared sections was fixed on a slide glass. Each slide glass was dipped in xylene for deparaffinization and then in methanol containing 0.3% hydrogen peroxide for 30 minutes and then washed by dipping in PBS for 30 minutes. Subsequently, 10% rabbit normal serum (Nichirei Corporation) was applied onto the thus washed section on each slide glass. After incubation for 1 hour, the sections were washed in PBS. Culture supernatant from a 3-day culture of the hybridoma HIK-1083 (Accession number P-13622) in normal medium [RPMI 1640 (Nissui Pharmaceutical Co., Ltd.) (10.2 g/l) medium supplemented with sodium hydrogen carbonate (2.2 g/l), L-glutamine (0.3 g/l), gentamycin (40 mg/l) and fetal calf serum (10% V/V)] was then applied onto the washed section on each slide glass. After incubation for 1 hour, the sections were washed in PBS. Biotin-labeled rabbit anti-mouse IgG+IgA+IgM (H+L) (Nichirei Corporation) was applied onto each washed section. After incubation for 1 hour, the sections were washed in PBS. Peroxidase-conjugated streptavidin (Nichirei Corporation) was then applied onto each washed section. After incubation for 1 hour, the sections were washed in PBS. Subsequently, each washed section was dipped for about 4 minutes in 0.05M Tris-HCl buffer, pH 7.6, containing 0.02% diaminobenzidine (Dojindo Laboratories) and 0.005% aqueous hydrogen peroxide, for color development. The results were as shown in Table 1.

These results show that human gastric gland-type mucus (class III mucus) can be specifically detected by using the monoclonal antibody obtained in Example 1.

TABLE 1

| Gastric mucosa | Corpus | Mucus gel layer | + |
|---|---|---|---|
| | | Surface mucous cell | − |
| | | Mucous neck cell | + |
| | Antrum | Mucus gel layer | + |
| | | Surface mucous cell | − |
| | | Pyloric gland cell | + |
| Duodenal mucosa | | Villus epithelium | − |
| | | Brunner's gland | + |

N.B.
+: positive to staining;
−: negative to staining (2) Analysis of components The mucus glycoprotein antigen with which the monoclonal antibody obtained in Example 1 reacted specifically was analyzed.

(a) Preparation of mucus glycoprotein decomposition product

Pig gastric mucus glycoprotein (Sigma) was subjected, in accordance with the procedure as described in Carlson, Don M. (1968) J. Biol. Chem. 243, 616–626, to 24-hour heat treatment at 50° C. in 0.05M aqueous sodium hydroxide solution containing 1M sodium borohydride.

(b) Separation and purification of the decomposition product mentioned above

The reaction solution obtained in (a) above was cooled down to room temperature and applied to a column TOYO-PEARL HW-50S, a hydrophilic vinyl polymer based filler (Tosoh Corporation) pre-equilibrated with 0.1N acetic acid. The column was eluted with 0.5N acetic acid and the eluate was fractionated into 40 fractions. The resultant fractions were assayed for antigenic activity by the Competitive ELISA as described below and the fractions with antigenic activity which were eluted latest were selected. The thus selected fractions were further fractionated into 70 fractions by means of HPLC using a TSK gel $NH_2$-60 a silica gel filler chemically bonded with amino propyl groups column (Tosoh Corporation) and each fraction was assayed for antigenic activity by the Competitive ELISA as described below. Among the resultant 70 fractions, three fractions showing stronger antigenic activity were selected and these three fractions were combined and evaporated to dryness in vacuo.

Competitive ELISA: The purified mucus glycoprotein antigen was dissolved in 0.05M sodium carbonate-sodium hydrogen carbonate buffer, pH 9.6, at a concentration of 2 µg/ml. 100 µl of the solution was added to each well of a microplate adapted for use in ELISA (Corning) and was allowed to stand overnight at 4° C. Each well was washed three times with 0.05% TWEEN 20 in PBS (PBS-TWEEN), filled with 2% skim milk in PBS and then allowed to stand for 1 hour. The wells were washed three times with PBS-TWEEN. In a separate container, 50 µl of the sample, i.e. the above-mentioned column eluate of mucus glycoprotein antigen decomposition product, 25 µl of culture supernatant from a 3-day culture of hybridoma HIK-1083 (Accession number P-13622) in normal medium [RPMI 1640 (Nissui Pharmaceutical Co., Ltd. ) (10.2 g/l) medium supplemented with sodium hydrogen carbonate (2.2 g/l), L-glutamine (0.3 g/l), gentamycin (40 mg/l) and fetal calf serum (10% V/V)] and 25 µl of a 4-fold concentrate of PBS were mixed together and the mixture was allowed to stand for 2 hours. These mixture were added to the washed wells. After incubation for 1 hour, the wells were washed three times with PBS-TWEEN, and 100 µl of a 1:10,000 dilution in PBS of peroxidase-conjugated goat anti-mouse immunoglobulins antibody (Tago, Inc.) was added as secondary antibody to each well. After 1 hour of incubation, the wells were washed three times with PBS-TWEEN and 100 µl of an ABTS-$H_2O_2$ peroxidase substrate solution (Kirkegaard & Perry Laboratories) was added to each well. After 30 minutes of incubation at room temperature, the optical density at 415 nm was measured for each well using a microplate reader. Those samples corresponding to the wells which gave lower optical density than that of the reaction solution in the well where the above-described procedure was performed using distilled water instead of the samples were judged as ones having antigenic activity.

(c) Analysis of product obtained by evaporation to dryness in vacuo

The product obtained in (b) above by evaporation to dryness in vacuo was trimethylsilylated in accordance with the method of Sweeley et al. (Sweeley, C. C. (1963) J. Am. Chem. Soc. 85, 2497–2507) and then analyzed by gas chromatography. Thus, the above-mentioned product was subjected to heat treatment in methanol containing 3% HCl and silver carbonate was added to the reaction solution to adjust the pH to 5. Subsequently acetic anhydride was added to the reaction solution and the mixture was allowed to stand overnight at room temperature. The mixture was then centrifuged at 2,000 rpm for 5 minutes and the supernatant was removed and evaporated to dryness in vacuo. A TRI-SIL, hexamethyldisilazane, trimethylchlorosilane and high purity grade pyridine (2:1:10) reagent (Pierce) was added to dissolve in the resultant concentrated residue. After incubation, aliquots of the reaction solution were injected into a Model "GC7A gas chromatograph (Shimazu Corporation) equipped with an OV-1 (dimethyl silicone gum) capillary column (GL Science Inc.) measuring 2.5 m in length and 0.25 mm in inner diameter, followed by detection using an FID (frame-ionization detector). The detected peaks were identified by comparison with chromatograms obtained with standard substances under the same analytical conditions. The standard substances were prepared by reacting a TRI-SIL reagent (Pierce) with fucose, galactose, glucose, mannose, N-acetylgalactosamine or N-acetylglucosamine. Furthermore, N-acetylgalactosaminitol standard substance was prepared by reduction of N-acetylgalactosamine in 0.2M borate buffer, pH 9, containing sodium borohydride, followed by reaction with a TRI-SIL reagent (Pierce). There were thus detected, from the concentrated residue of the above described fractions with antigenic activity, N-acetylgalactosaminitol, N-acetylglucosamine, fucose and galactose.

Example 3

Reactivity with sugars

For each of methyl 2-acetamido-2-deoxy-α-D-glucopyranoside (Sigma) and methyl 2-acetamido-2-deoxy-β-D-glucopyranoside (Sigma), a 1 mg/ml solution in distilled water was prepared and two-fold serial dilutions were prepared therefrom using distilled water. The reactivity of the monoclonal antibody obtained in Example 1 with these aqueous solutions were examined by the Competitive ELISA as described below. As a result, the methyl 2-acetamido-2-deoxy-α-D-glucopyranoside decreased the optical density in dependence upon its concentration and hence the reactivity therewith was observed, whereas no such concentration-dependent change in the optical density was found with the methyl 2-acetamido-2-deoxy-β-D-glucopyranoside.

Competitive ELISA: The purified mucus glycoprotein antigen was dissolved in 0.05M sodium carbonate-sodium hydrogen carbonate buffer, pH 9.6, at a concentration of 2 µg/ml. 100 µl of the solution was added to each well of a microplate adapted for use in ELISA (Corning) and was allowed to stand overnight at 4° C. Each well was washed three times with 0.05% TWEEN 20 in PBS (PBS-TWEEN), filled with 2% skim milk in PBS and then allowed to stand for 1 hour. The wells were washed three times with PBS-TWEEN. In a separate container, 50 µl of the sample, i.e. the above described aqueous solution, 25 µl of culture supernatant from a 3-day culture of hybridoma HIK-1083 (Accession number P-13622) in normal medium [RPMI 1640 (Nissui Pharmaceutical Co., Ltd.) (10.2 g/l) medium supplemented with sodium hydrogen carbonate (2.2 g/l), L-glutamine (0.3 g/l), gentamycin (40 mg/l) and fetal calf serum (10% V/V)] and 25 µl of 4-fold concentrate of PBS were mixed together and the mixture was allowed to stand for 2 hours. These mixtures were added to the washed wells. After incubation for 1 hour, the wells were washed three times with PBS-TWEEN, and 100 µl of a 1:10,000 dilution in PBS of peroxidase-conjugated goat anti-mouse immunoglobulins antibody (Tago, Inc.) was added as secondary antibody to each well. After 1 hour of incubation, the wells were washed three times with PBS TWEEN and 100 µl of an ABTS-$H_2O_2$ peroxidase substrate solution (Kirkegaard & Perry Laboratories) was added to each well. After 30 minutes of incubation at room temperature, the optical density at 415 nm was measured for each well using a microplate reader.

We claim:

1. An IgM class monoclonal antibody which specifically reacts with Class III mucus glycoproteins and which does not react with human gastric surface mucous cells or the mucus glycoproteins secreted thereby.

2. The monoclonal antibody of claim 1, wherein the IgM class monoclonal antibody is produced by a hybridoma deposited in the National Institute of Bioscience and Human-Technology (NIBH), Agency of Industrial Science and Technology with the accession number P-13622.

3. A hybridoma which produces an IgM class monoclonal antibody with specific reactivity with Class III mucus glycoproteins and no reactivity with human gastric surface mucous cells or the mucus secreted thereby.

4. A hybridoma deposited in the National Institute of Bioscience and Human-Technology (NIBH), Agency of Industrial Science and Technology with the accession number P-13622.

5. A method of determining the presence or amount of Class III mucus glycoproteins comprising:

obtaining a sample of human body fluid;

contacting said sample with the monoclonal antibody of claim 1; measuring formation of any specific binding complexes comprising the monoclonal antibody of claim 1; and correlating the presence or amount of said specific binding complexes to the presence or amount of said class III mucus glycoproteins in said sample.

* * * * *

UNITED STATES PATENT AND TRADEMARK OFFICE
CERTIFICATE OF CORRECTION

PATENT NO. : 5,576,182
DATED : Nov. 19, 1996
INVENTOR(S) : Kurihara et al.

It is certified that error appears in the above-indentified patent and that said Letters Patent is hereby corrected as shown below:

On the title page:

Item [86] please change the §371 date from "Jan. 19, 1995" to --Jan. 18, 1995--; and please change the §102(e) date from "Jan. 19, 1995" to --Jan. 18, 1995--.

Signed and Sealed this

First Day of April, 1997

*Attest:*

BRUCE LEHMAN

*Attesting Officer*     *Commissioner of Patents and Trademarks*